United States Patent [19]
Arnold et al.

[11] 4,128,728
[45] Dec. 5, 1978

[54] PRODUCTION OF 2,3,6-TRIMETHYLPHENOL

[75] Inventors: Lothar Arnold, Heidelberg; Heinrich Pasedach; Horst Pommer, both of Ludwigshafen, all of Fed. Rep. of Germany

[73] Assignee: Badische Anilin- & Soda-Fabrik Aktiengesellschaft, Ludwigshafen am Rhein, Fed. Rep. of Germany

[21] Appl. No.: 804,282

[22] Filed: Mar. 4, 1969

[30] Foreign Application Priority Data

Mar. 8, 1968 [DE] Fed. Rep. of Germany ....... 1668874
Jul. 26, 1968 [DE] Fed. Rep. of Germany ....... 1793037

[51] Int. Cl.$^2$ .............. C07C 37/06; C07C 45/00
[52] U.S. Cl. ................................ 568/799; 260/586 C
[58] Field of Search ............ 260/621 H, 586 R; 568/799

[56] References Cited

U.S. PATENT DOCUMENTS

| | | | |
|---|---|---|---|
| 2,640,084 | 5/1953 | Chitwood et al. | 260/621 H |
| 3,194,843 | 7/1965 | Silber et al. | 260/621 H |

OTHER PUBLICATIONS

Levenspiel, "Chemical Reaction Engineering", pp. 327-328, 1962.
Cope et al., "Organic Reactions", vol. 16, pp. 28-30, 1968.
Lacey, "J. Chem. Soc." vol. 1960, pp. 1639-1648 (1960).
Chapwilat, "Comptes Rendus" vol. 253, pp. 2261-2263 (1961).
Colonge, "Comptes Rendus" vol. 251, pp. 252-254 (1960).
Horning et al., "J.A.C.S.," vol. 71, pp. 169-171 (1949).
Lacey, "J. Chem. Soc.," vol. 1, 1960, pp. 1639-1648.

*Primary Examiner*—Norman Morgenstern
*Attorney, Agent, or Firm*—Keil, Thompson & Shurtleff

[57] ABSTRACT

A process for the production of 2,3,6-trimethylphenol in which diethyl ketone is reacted in the presence of a basic reagent with crotonaldehyde or methyl vinyl ketone (or a compound which in the presence of a basic reagent is converted into crotonaldehyde or methyl vinyl ketone) and the 2,5,6-trimethyl-2-cyclohexen-1-one or 2,3,6-trimethyl-2-cyclohexen-1-one formed is dehydrogenated.

10 Claims, No Drawings

PRODUCTION OF 2,3,6-TRIMETHYLPHENOL

The present invention relates to a new process for the production of 2,3,6-trimethylphenol.

2,3,6-trimethylphenol is known to be an important intermediate for the synthesis of vitamin E.

In the prior art methods for the production of 2,3,6-trimethylphenol the starting materials used are benzene derivatives such as pseudocumene or dimethylphenols. These methods are very expensive however because isomer mixtures are formed from which the desired isomers can be recovered in pure form only with difficulty and with losses being incurred.

It is an object of the invention to provide a process for the production of 2,3,6-trimethylphenol in which readily accessible starting materials are used. Another object of the invention is to provide a process in which 2,3,6-trimethylphenol is obtained in good yields and high purity.

In accordance with this invention these and other objects and advantages are achieved in a process for the production of 2,3,6-trimethylphenol in which diethyl ketone is reacted in the presence of a basic reagent with crotonaldehyde or methyl vinyl ketone or a compound which in the presence of a basic reagent is converted into crotonaldehyde or methyl vinyl ketone and the resultant 2,5,6-trimethyl-2-cyclohexen-1-one or 2,3,6-trimethyl-2-cyclohexen-1-one is dehydrogenated.

When crotonaldehyde is used as starting material the reaction may be represented by the following equation:-

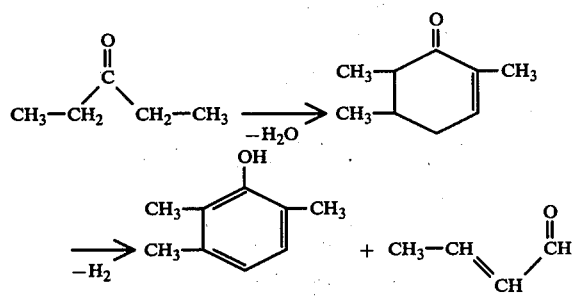

It is surprising that derivatives of cyclohexen-1-one can be prepared by the process according to this invention in a smooth reaction because it is known from the articles by J. Colonge et al., Bull. soc. chim. France, 1954, page 1444 and Bull. soc. chim. France, 1959, page 450 that derivatives of cyclohexen-2-one-1 are obtained only when using methyl ketones but not when using diethyl ketone and that when methyl ketones are used yields of cyclohexenone of 40% at the most are achieved.

Compounds which in the presence of a basic reagent are converted into crotonaldehyde or methyl vinyl ketone include butyraldehydes or methyl ethyl ketones which bear in β-position to the keto group a substituent which by the action of a basic reagent is eliminated together with a hydrogen atom in α-position. Examples of such substituents are hydroxy, alkoxy, aryloxy, alkylmercapto, arylmercapto, acyloxy or dialkylamino groups, halogen atoms or radicals of salts known as onium salts, such as the radical of a quaternary ammonium salt or of a trialkylsulfonium salt. In the case of radicals containing alkyl substituents, alkyl substituents having from one to six carbon atoms are preferred. Examples of suitable butyraldehydes are: β-hydroxybutyraldehyde, β-methoxybutyraldehyde, β-phenoxybutyraldehyde, β-acetyloxybutyraldehyde, β-benzyloxybutyraldehyde, β-methylsulfonyloxybutyraldehyde, β-dimethylaminobutyraldehyde and β-chlorobutyraldehyde.

Examples of suitable methyl ethyl ketones are: methyl β-hydroxyethyl ketone, methyl β-methoxyethyl ketone, methyl β-phenoxyethyl ketone, methyl β-acetyloxyethyl ketone, methyl β-benzoyloxyethyl ketone, methyl β-methylsulfonyloxyethyl ketone, methyl β-phenylsulfonyloxyethyl ketone, methyl β-dimethylaminoethyl ketone, methyl β-chloroethyl ketone, dimethyl-(β-acetylethyl)-sulfonium bromide and trimethyl-(β-acetylethyl)-ammonium iodide. For reasons of economy, methyl β-hydroxyethyl ketone is preferred among the methyl ethyl ketones.

Examples of basic reagents which may be used are: alkali metals, alkaline earth metals, the hydroxides, oxides, alcoholates, amides, hydrides, carbonates or organometallic compounds of the alkali metals and alkaline earth metals, or quaternary ammonium hydroxides. Specific examples are: sodium hydroxide, potassium hydroxide, calcium hydroxide, sodium carbonate, potassium carbonate, sodium methylate, sodium amide, sodium hydride, sodium, phenyllithium, methyllithium and tetramethylammonium hydroxide.

Condensation of the starting materials may be carried out in a solvent or in the absence of a solvent. When no solvent is added, it is advantageous to use an excess of diethyl ketone as a diluent. Examples of solvents are organic solvents such as aliphatic or aromatic hydrocarbons, ethers, sulfoxides, preferably alcohols and water. Of the alcohols those are preferred which have one to ten, particularly one to six, carbon atoms. Specific examples of suitable solvents are ligroin, benzene, toluene, diethyl ether, tetrahydrofuran, dimethyl sulfoxide, methyl glycol, methanol, ethanol, isopropanol, isobutanol, and ethylene diglycol. Generally the weight ratio of solvent to crotonaldehyde or methyl vinyl ketone or their precursors is from 1:10 to 10:1.

Condensation is generally carried out at temperatures of from −20° to 200° C., preferably from +20° to 150° C. Atmospheric pressure is used as a rule, but subatmospheric pressure, for example 100 mm Hg, or superatmospheric pressure, for example the pressure set up when using a solvent which has a boiling point lower than the reaction temperature, may be used.

Diethyl ketone and crotonaldehyde, methyl vinyl ketone or their precursors may be reacted in the molar ratio of from 1:1 to 50:1, preferably from 2:1 to 10:1. The amount of basic reagent may be varied within wide limits. Generally it is used in an amount of from 0.1% of the equivalent amount to the equivalent amount with reference to crotonaldehyde and methyl vinyl ketone.

When using compounds which can be converted by the action of basic reagents into methyl vinyl ketone or crotonaldehyde, an additional amount of alkali required for elimination to give the double bond is used.

Condensation may for example be carried out by mixing diethyl ketone, a basic reagent and any solvent used and adding crotonaldehyde, methyl vinyl ketone or a precursor thereof at the reaction temperature at the rate at which it is used up. The crotonaldehyde, methyl vinyl ketone or precursor thereof may advantageously be diluted with solvent or extra diethyl ketone, prior to addition to the mixture.

It may also be advantageous to stabilize these starting materials by adding a polymerization inhibitor such as hydroquinone or hydroquinone monomethyl ether. Water formed in the reaction may be removed from the reaction mixture, for example by separating it together with a suitable diluent such as benzene or toluene or with excess diethyl ketone as an azeotrope, the diluent being recycled if desired.

Reaction generally takes from fifteen minutes to five hours depending on the reaction temperature.

The reaction mixture may be processed for example by first neutralizing it and then separating the 2,5,6-trimethyl-2-cyclohexen-1-one or 2,3,6-trimethyl-2-cyclohexen-1-one from any excess diethyl ketone and solvent added by fractional distillation.

When methyl vinyl ketone or its precursors are reacted, more or less large amounts of 4-methyl-3-ethyl-2-cyclohexen-1-one are obtained as byproduct depending on the reaction conditions. However, this can be rearranged in conventional manner by treatment with aqueous bases, for example aqueous caustic soda or caustic potash solution, that after equilibrium has been set up a mixture of about 96% by weight of 2,3,6-trimethyl-2-cyclohexen-1-one and about 4% by weight of the byproduct is formed. It is therefore possible by isomerization to convert the byproduct almost quantitatively into the isomeric 2,3,6-trimethyl-2-cyclohexen-1-one.

Isomerisation may be carried out for example by separating the 4-methyl-3-ethyl-2-cyclohexen-1-one from the reaction mixture by fractional distillation and then treating it with aqueous caustic soda solution, for example a 10% by weight solution, at elevated temperature, for example at refluxing temperature. The mixture of isomers is then advantageously separated by fractional distillation and the compound which has not been rearranged is again isomerized. Isomerization may however also be carried out by treating the reaction mixture obtained in the condensation for some time, for example five hours, at elevated temperature with an aqueous base.

The 2,5,6-trimethyl-2-cyclohexen-1-one or 2,3,6-trimethyl-2-cyclohexen-1-one obtained is then dehydrogenated to 2,3,6-trimethylphenol in known manner (cf. for example U.K. Patent Specification No. 951,435), for example in liquid phase by heating with sulfur, selenium or chloranil and either in liquid phase or in gas phase by heating in the presence of metals of group 8 of the Periodic System, such as iron, cobalt, nickel, rhodium, platinum, palladium or metals oxides of metals of subgroup 1 of the Periodic System, such as copper or silver. It is preferred to use metals of group 8 and subgroup 1 of the Periodic System, particularly palladium. The metallic dehydrogenation catalysts are advantageously used on a conventional carrier such as aluminum oxide, silica gel or activated carbon.

Dehydrogenation may be carried out in an inert solvent. It is advantageous however to dehydrogenate the 2,5,6-trimethyl-2-cyclohexen-1-one or 2,3,6-trimethyl-2-cyclohexen-1-one in the gas phase, for example by passing it as a gas at the dehydrogenation temperature over a palladium/silica gel catalyst. In gas-phase dehydrogenation the trimethyl-2-cyclohexen-1-one is preferably passed over the catalyst in admixture with an extraneous gas such as nitrogen, steam, carbon dioxide and particularly hydrogen; generally a ratio by volume of extraneous gas to gaseous trimethyl-2-cyclohexen-1-one of from about 1:2 to 5:1 is chosen. Temperatures of from 200° to 400° C., preferably from 250° to 350° C., are usually used in gas-phase dehydrogenation. The time that the trimethyl-2-cyclohexen-1-one is in contact with the catalyst is generally from half to fifty, preferably from two to ten seconds. The 2,3,6-trimethylphenol is obtained in a more than 95% yield in gas-phase dehydrogenation.

The following Examples illustrate the invention.

EXAMPLE 1

70 g of crotonaldehyde is dripped in the course of half an hour into a mixture of 1000 g of diethyl ketone, 250 g of isobutanol and 5 g of 50% caustic soda solution which is boiling under reflux. The whole is then boiled for another half hour. The whole is neutralized with glacial acetic acid and the aqueous layer formed is removed. Excess diethyl ketone and isobutanol are separated by fractional distillation and then 106 g of 2,5,6-trimethyl-2-cyclohexen-1-one distils at a temperature of from 74° to 76° C. at 12 mm Hg. The yield is 77% with reference to crotonaldehyde.

EXAMPLE 2

70 g of crotonaldehyde is dripped in the course of one hour into a mixture of 400 g of diethyl ketone and 10 g of a 30% solution of sodium methylate in methanol which is boiling under reflux and the reaction mixture is boiled for another half hour under reflux. The whole is neutralized with glacial acetic acid and the mixture obtained is filtered. 325 g of diethyl ketone is recovered by distillation of the filtrate; 55 g of 2,5,6-trimethyl-2-cyclohexen-1-one having a boiling point of from 74° to 76° C. at 12 mm Hg is obtained. The yield with reference to crotonaldehyde is 40%.

EXAMPLE 3

A mixture of 88 g of β-hydroxybutyraldehyde and 150 g of diethyl ketone is added dropwise in the course of one hour to a mixture of 250 g of diethyl ketone, 80 g of isopropanol and 5 g of sodium hydroxide powder which is boiling under reflux. The whole is boiled for another hour under reflux. Neutralization is effected with glacial acetic acid and the aqueous phase is separated. The organic layer is fractionated. 65 g of 2,5,6-trimethyl-2-cyclohexen-1-one having a boiling point of 74° to 76° C. at 12 mm Hg is obtained. The yield is 47% with reference to β-hydroxybutyraldehyde.

EXAMPLE 4

102 g of β-methoxybutyraldehyde is dripped in the course of one hour into a mixture of 500 g of diethyl ketone and 10 g of a 30% solution of sodium methylate in methanol which is boiling under reflux. The whole is then heated for another hour under reflux. The reaction mixture is processed as described in Example 2. 77 g of 2,5,6-trimethyl-2-cyclohexen-1-one is obtained, i.e. a 56% yield with reference to β-methoxybutyraldehyde.

EXAMPLE 5

1000 g of 2,5,6-trimethyl-2-cyclohexen-1-one is passed per hour per liter of catalyst at atmospheric pressure through an externally heated tube having a capacity of 250 $cm^3$ and filled with a palladium/silica gel catalyst (0.2% by weight of palladium), the temperature being 300° C. The yield is 96% of 2,3,6-trimethylphenol. 4% of starting material is recovered and returned to the reaction.

EXAMPLE 6

1000 g of 2,5,6-trimethyl-2-cyclohexen-1-one is passed, at 300° C. per hour per liter of catalyst at atmospheric pressure, through an externally heated tube having a capacity of 250 ccm and filled with a platinum/carbon catalyst (0.2% by weight of platinum). The yield of 2,3,6-trimethylphenol is 92%.

EXAMPLE 7

The procedure of Example 5 is followed but the palladium catalyst is replaced by a catalyst consisting of 100 parts by weight of carbon, 8 parts by weight of nickel, 3 parts by weight of copper and 1 part by weight of chromium. 500 g of 2,5,6-trimethyl-2-cyclohexen-1-one is passed over the catalyst at 350° C. per hour per liter of catalyst in admixture with hydrogen (molar ratio of hydrogen to cyclohexenone 2:1). The yield of 2,3,6-trimethylphenol is 89%.

EXAMPLE 8

A mixture of 70 g of methyl vinyl ketone, 200 g of diethyl ketone and 0.1 g of hydroquinone is dripped in the course of one hour into a mixture of 1000 g of diethyl ketone and 5 g of sodium hydroxide powder which is boiling under reflux. The reaction mixture is heated under reflux for another half hour. Water formed in the reaction is removed from the reaction mixture, by means of a water entrainer, 17 g of water thus being separated. Neutralization is effected with glacial acetic acid and the mixture is filtered and distilled. 1120 g of diethyl ketone is recovered. Fractional distillation of the residue gives 81 g of 2,3,6-trimethyl-2-cyclohexen-1-one having a boiling point of 89° C. at 12 mm Hg and 29 g of 4-methyl-3-ethyl-2-cyclohexen-1-one having a boiling point of 102° C. at 12 mm Hg. The total yield of cyclohexenone is 80% with reference to methyl vinyl ketone.

EXAMPLE 9

A mixture of 70 g of methyl vinyl ketone, 10 g of water and 0.1 g of hydroquinone is dripped in the course of one hour into a mixture of 400 g of diethyl ketone and 10 g of a 30% by weight methanolic solution of sodium methylate which is boiling under reflux. The whole is then heated for another two hours under reflux. The mixture obtained is neutralized with glacial acetic and then filtered. Excess diethyl ketone and the water present are distilled off and the residue is fractionated in vacuo. 81 g of 2,3,6-trimethyl-2-cyclohexen-1-one having a boiling point of 89° C. at 12 mm Hg and 9 g of 4-methyl-3-ethyl-2-cyclohexen-1-one having a boiling point of 102° C. at 12 mm Hg are obtained. The total yield of cyclohexenone is 65% with reference to methyl vinyl ketone.

EXAMPLE 10

A mixture of 88 g of 3-ketobutan-1-ol, 150 g of diethyl ketone and 0.1 g of hydroquinone is dripped in the course of two hours into a mixture of 250 g of diethyl ketone and 10 g of a 30% by weight solution of sodium methylate in methanol which is boiling under reflux. The reaction mixture is then heated under reflux for another two hours. 37 g of water is removed from the reaction mixture by entrainment during the reaction. The whole is processed as described in Example 8. 73 g of 2,3,6-trimethyl-2-cyclohexen-1-one and 10 g of 4-methyl-3-ethyl-2-cyclohexen-1-one are obtained. The total yield of cyclohexenone is 60% with reference to 3-ketobutan-1-ol.

EXAMPLE 11

A mixture of 138 g of 4-methyl-3-ethyl-2-cyclohexen-1-one and 500 g of 7% by weight caustic soda solution is heated under reflux for five hours. After the reaction mixture has cooled, the cyclohexenone mixture formed is taken up in 500 ml of hexane and separated from the aqueous layer. Hexane is distilled off from the organic phase obtained. 135 g of a residue is obtained which consists of 96% of 2,3,6-trimethyl-2-cyclohexen-1-one and 4% of 4-methyl-3-ethyl-2-cyclohexen-1-one.

EXAMPLE 12

152 g of 1-methoxybutan-3-one is dripped in the course of one hour into a boiling mixture of 400 g of diethyl ketone and 5 g of a 30% by weight solution of sodium methylate in methanol. The whole is then heated under reflux for another hour. The reaction mixture is neutralized with glacial acetic acid and then fractionated. 70 g of 2,3,6-trimethyl-2-cyclohexen-1-one and 9 g of 4-methyl-3-ethyl-2-cyclohexen-1-one is obtained. The total yield of cyclohexenone is 57% with reference to 1-methoxybutan-3-one.

EXAMPLE 13

130 g of 1-acetoxybutan-3-one and sodium methylate solution in methanol are dripped in the course of one hour from separate supply vessels while stirring into 400 g of boiling diethyl ketone at such a rate that the reaction mixture remains constantly alkaline. A total of 190 g of a 30% by weight sodium methylate solution is used up in this way. The whole is then heated under reflux for another hour and then neutralized with glacial acetic acid. Deposited sodium acetate is filtered off and the filtrate is subjected to fractional distillation. 81 g of 2,3,6-trimethyl-2-cyclohexen-1-one is obtained as well as traces of 4-methyl-3-ethyl-2-cyclohexen-1-one. The yield with reference to 1-acetoxybutan-3-one is 59%.

EXAMPLE 14

The procedure of Example 13 is followed but 107 g of 1-chlorobutan-3-one is used instead of 1-acetoxybutan-3-one. 76 g of 2,3,6-trimethyl-2-cyclohexen-1-one and traces of 4-methyl-3-ethyl-2-cyclohexen-1-one are obtained. The yield is 55% with reference to 1-chlorobutan-3-one.

EXAMPLE 15

The procedure of Example 12 is followed but 115 g of 1-dimethylaminobutan-3-one is used instead of 1-methoxybutan-3-one. 78 g of 2,3,6-trimethyl-2-cyclohexen-1-one and 7 g of 4-methyl-3-ethyl-2-cyclohexen-1-one are obtained. The yield of cyclohexenone is 62% with reference to 1-dimethylaminobutan-3-one.

EXAMPLE 16

An externally heated tube having a capacity of 250 cm$^3$ is filled with a catalyst of 0.07% by weight of palladium on silica gel and 1000 g of 2,3,6-trimethyl-2-cyclohexen-1-one per liter of catalyst per hour is passed through at atmospheric pressure and 300° C. The yield of 2,3,6-trimethylphenol is 95%. 5% of starting material is recovered and returned to the reaction.

EXAMPLE 17

An externally heated tube having a capacity of 250 cm³ is filled with a catalyst of 0.2% by weight of platinum on carbon and 1000 g of 2,3,6-trimethyl-2-cyclohexen-1-one per liter of catalyst per hour is passed through at atmospheric pressure and 300° C. The yield of 2,3,6-trimethylphenol is 92%.

EXAMPLE 18

The procedure of Example 17 is followed but a catalyst containing 100 parts by weight of carbon, 8 parts by weight of nickel, 3 parts by weight of copper and 1 part by weight of chromium is used instead of the platinum catalyst. 500 g of 2,3,6-trimethyl-2-cyclohexen-1-one per liter of catalyst per hour mixed with hydrogen (molar ratio of hydrogen to cyclohexenone 2:1) is passed over the catalyst at 350° C. The yield of 2,3,6-trimethylphenol is 89%.

We claim:

1. A process for the production of 2,3,6-trimethylphenol which comprises reacting a carbonyl compound selected from the group consisting of methyl vinyl ketone, methyl β-hydroxyethyl ketone, methyl β-methoxyethyl ketone, methyl β-phenoxyethyl ketone, methyl β-acetyloxyethyl ketone, methyl β-benzoyloxyethyl ketone, methyl β-methyl-sulfonyloxyethyl ketone, methyl β-phenylsulfonyloxyethyl ketone, methyl β-dimethylaminoethyl ketone, methyl β-chloroethyl ketone, dimethyl-(β-acetylethyl)-sulfonium bromide or trimethyl-(β-acetylethyl)-ammonium iodide to a mixture of diethyl ketone and a basic reagent selected from the group consisting of an alkali metal, an alkaline earth metal, a hydroxide, oxide, alcoholate, amide, hydride or organo metallic compound of an alkali metal or alkaline earth metal, and a quaternary ammonium hydroxide, the amount of said diethyl ketone being in the molar ratio of 1:1 to 50:1 with respect to the total amount of carbonyl compound added, at a reaction temperature of 20° to 150° C. to produce 2,3,6-trimethyl-2-cyclohexen-1-one, and dehydrogenating the latter to produce 2,3,6-trimethylphenol.

2. A process as claimed in claim 1 wherein said diethyl ketone is reacted with methyl vinyl ketone.

3. A process as claimed in claim 1 wherein diethyl ketone is reacted with one of said methyl ethyl ketones.

4. A process as claimed in claim 1 wherein said diethyl ketone is reacted with methyl β-hydroxyethyl ketone.

5. A process as claimed in claim 1 wherein said carbonyl compound is methyl vinyl ketone and the amount of said basic reagent in the reaction mixture is from 0.1% of the equivalent amount up to the equivalent amount with reference to the methyl vinyl ketone.

6. A process as claimed in claim 1, said basic reagent being a member selected from the group consisting of sodium hydroxide, potassium hydroxide, calcium hydroxide, sodium carbonate, potassium carbonate, sodium methylate, sodium amide, sodium hydride, sodium, phenyllithium, methyllithium and tetramethylammonium hydroxide.

7. A process for producing 2,3,6-trimethyl-2-cyclohexen-1-one comprising condensing diethyl ketone with methyl vinyl ketone in the presence of a base selected from the group consisting of an alkali metal, an alkaline earth metal, a hydxoxide, oxide, alcoholate, amide, hydride or organo metallic compound of an alkali metal or alkaline earth metal, and a quaternary ammonium hydroxide.

8. A process as claimed in claim 7 wherein said diethyl ketone is present in the reaction mixture in the amount of 1-50 moles per mole of said methyl vinyl ketone.

9. A process as claimed in claim 7 wherein said base is an alkali methyl hydroxide.

10. A process as claimed in claim 7 wherein said base is a member selected from the group consisting of sodium hydroxide, potassium hydroxide, calcium hydroxide, sodium carbonate, potassium carbonate, sodium methylate, sodium amide, sodium hydride, sodium, phenyllithium, methyllithium and tetramethylammonium hydroxide.

* * * * *